(12) United States Patent
Meythaler et al.

(10) Patent No.: US 8,513,281 B1
(45) Date of Patent: Aug. 20, 2013

(54) METHOD OF TREATING TRAUMATIC BRAIN AND SPINAL CORD INJURIES AND OTHER NEUROGENIC CONDITIONS USING NON-STEROIDAL ANTI-INFLAMMATORY DRUGS AND NATURALLY OCCURRING CONOTOXINS

(75) Inventors: Jay M. Meythaler, Birmingham, AL (US); Jean Peduzzi, Chelsea, AL (US)

(73) Assignee: Landon C. G. Miller, Tuscaloosa, AL (US)

( * ) Notice: Subject to any disclaimer, the term of this patent is extended or adjusted under 35 U.S.C. 154(b) by 822 days.

(21) Appl. No.: 10/049,327

(22) PCT Filed: Aug. 10, 2000

(86) PCT No.: PCT/US00/21893
§ 371 (c)(1),
(2), (4) Date: May 15, 2002

(87) PCT Pub. No.: WO01/10455
PCT Pub. Date: Feb. 15, 2001

Related U.S. Application Data

(60) Provisional application No. 60/148,068, filed on Aug. 10, 1999.

(51) Int. Cl.
*A61K 31/495* (2006.01)
*A61P 3/10* (2006.01)
*A61P 3/06* (2006.01)
*A61P 27/02* (2006.01)

(52) U.S. Cl.
USPC ............ 514/310; 514/159; 514/164; 514/169

(58) Field of Classification Search
USPC .................................. 514/164–169, 159, 310
See application file for complete search history.

(56) References Cited

U.S. PATENT DOCUMENTS

| | | | |
|---|---|---|---|
| 4,447,356 A | 5/1984 | Olivera et al. | 260/112.5 |
| 5,189,020 A | 2/1993 | Miljanich et al. | 514/12 |
| 5,192,753 A * | 3/1993 | McGeer et al. | 514/159 |
| 5,223,409 A | 6/1993 | Ladner et al. | 435/69.7 |
| 5,231,011 A | 7/1993 | Hillyard et al. | 435/69.7 |
| 5,264,371 A | 11/1993 | Miljanich et al. | 436/503 |
| 5,364,842 A | 11/1994 | Justice et al. | 514/12 |
| 5,386,025 A | 1/1995 | Jay et al. | 536/23.5 |
| 5,424,218 A | 6/1995 | Miljanich et al. | 436/503 |
| 5,429,921 A | 7/1995 | Harpold et al. | 435/4 |
| 5,432,155 A | 7/1995 | Olivera et al. | 514/12 |
| 5,474,547 A | 12/1995 | Aebischer et al. | 604/891.1 |
| 5,514,774 A | 5/1996 | Olivera et al. | 530/324 |
| 5,559,095 A | 9/1996 | Miljanich et al. | 514/12 |
| 5,562,907 A | 10/1996 | Arnon | 424/236.1 |
| 5,587,454 A | 12/1996 | Justice et al. | 530/324 |
| 5,589,340 A | 12/1996 | Olivera et al. | 435/6 |
| 5,591,821 A | 1/1997 | Olivera et al. | 530/324 |
| 5,595,972 A | 1/1997 | Olivera et al. | 514/13 |
| 5,633,347 A | 5/1997 | Olivera et al. | 530/324 |
| 5,643,960 A * | 7/1997 | Breitner et al. | 514/570 |
| 5,670,622 A | 9/1997 | Shon et al. | 530/324 |
| 5,672,682 A | 9/1997 | Terlau et al. | 530/324 |
| 5,677,288 A | 10/1997 | Marangos | 514/39 |
| 5,700,778 A | 12/1997 | Olivera et al. | 514/12 |
| 5,709,654 A | 1/1998 | Klatz et al. | 604/24 |
| 5,719,264 A | 2/1998 | Shon et al. | 530/324 |
| 5,739,276 A | 4/1998 | Shon et al. | 530/324 |
| 5,780,433 A | 7/1998 | McIntosh et al. | 514/13 |
| 5,795,864 A | 8/1998 | Amstutz et al. | 514/12 |
| 5,827,222 A | 10/1998 | Klatz et al. | 604/52 |
| 5,866,682 A | 2/1999 | McIntosh et al. | 530/326 |
| 5,885,780 A | 3/1999 | Olivera et al. | 435/7.1 |
| 5,914,129 A | 6/1999 | Mauskop | 424/464 |
| 6,043,224 A | 3/2000 | Lee et al. | 514/226 |
| 6,056,725 A | 5/2000 | Elsberry | 604/151 |
| 6,126,939 A * | 10/2000 | Eisenbach-Schwartz et al. | 424/185.1 |

FOREIGN PATENT DOCUMENTS

WO      WO 98/20864    *   5/1998

OTHER PUBLICATIONS

The Merck Index, Windholz et al Eds., Merck&Co., Rahway, N.J., astractNo. 2189.*
Uurna et al, 117CA:104057. 1992.*
Sakanashi et al, 95CA:161869, 1981.*
Bakhshi et al., "Implantable pumps for drug delivery to the brain" 1995, Journal of Neuro-Oncology, 26, 133-9.*
Bakhshi et al. Implantable pumps for drug delivery to the brain, Journal of Neuro-Oncology, 26, 133-9.*
Myseros et al. (The rationale for glutamate antagonists in the treatment of traumatic brain injury, Ann NY Acad Sci, 1995, 765:262-271).*
Wolff, Manfred E. "Burger's Medicinal Chemistry, 5ed, Part I", John Wiley & Sons, 1995, pp. 975-977.*
Bustamante, D., "Effects of Intrathecal or Intracerebroventricular Administration of Nonsteroidal Anti-inflammatory Drugs on a C-Fiber Reflex in Rats," The Journal of Pharmacology and Experimental Therapeutics, 281:1381-1391; 1997.

(Continued)

*Primary Examiner* — San-Ming Hui
*Assistant Examiner* — Kathrien Cruz

(57) ABSTRACT

A method for treating a patient/subject having neuronal injury, pain, neurotrauma and/or traumatic brain injury, such as diffuse axonal injury, which includes intrathecally and/or intraventricularly administering to the subject a therapeutically effective amount of a non-steroidal anti-inflammatory drug and/or a naturally occurring omega conotoxin, functional fragment thereof, a pharmacologically acceptable salt, ester, amide, or prodrug thereof.

7 Claims, 1 Drawing Sheet

(56) References Cited

OTHER PUBLICATIONS

Juurlink, B. et al., "Review of Oxidative Stress in Brain and Spinal Cord Injury: Suggestions for Pharmacological and Nutritional Management Strategies," The Journal of Spinal Cord Medicine, 21:309-334, 1998.

White, R.P., "Comparison of Piroxicam, Meclofenamate, Ibuprofen, Aspirin, and Prostacyclin Efficacy in a Chronic Model of Cerebral Vasospasm," Neurosurgery, L001 12(2), 40-46, Jan. 1983 (Abstract).

Segal, J., "4-Aminopyridine Alters Gait Characteristics and Enhances Locomotion in Spinal Cord Injured Humans," The Journal of Spinal Cord Medicine, 21:200-204, 1998.

Yamada, K., "W-Conotoxin GVIA Protects Against Ischemia-induced Neuronal Death in the Mongolian Gerbil but not Against Quinolinic Acid-induced Neurotoxicity in the Rat," Neuropharmacology, 33:251-254, 1994.

Shin, H. K., "Calcium Channel Blockers Suppress the Responses of Rat Dorsal Horn Cell to Nociceptive Input," Korean Journal of Physiology and Pharmacology, 1:625-637, 1997.

Wu, G., "Transient Brain Ischemis in Rabbits: The Effect of w-conopeptide MVIIC on Hippocampal Excitatory Amino Acids," Brain Research,118-122.

Valentino, K. et al., "A Selective N-Type Calcium Channel Antagonist Protects Against Neuronal Loss After Global Cerebral Ischemia," Proc. Natl. Acad. Sci. USA 90, 90:7894-7997; 1993.

Madden, K.P. et al., "Treatment with Conotoxin, an 'N-Type' Calcium Channel Blocker in Neuronal Hypoxic-Ischemic Injury," Brain Research, 537:256-262; 1990.

Database CA on STN. Chem. Abstr., vol. 117 (Columbus, OH, USA), Abstract No. 62794 Telpukhov et al. "Anti-ischemic brain protection with water soluble aspirin", Byull. Eksp. Biol. Med. 1992, 113(2), 156-459 (Russian).

\* cited by examiner

METHOD OF TREATING TRAUMATIC BRAIN AND SPINAL CORD INJURIES AND OTHER NEUROGENIC CONDITIONS USING NON-STEROIDAL ANTI-INFLAMMATORY DRUGS AND NATURALLY OCCURRING CONOTOXINS

FIELD OF THE INVENTION

The subject invention relates to the treatment of central nervous system injuries and/or conditions and, more particularly, the subject invention relates to the use of non-steroidal anti-inflammatory drugs for treatment of neurotrauma and neurogenic conditions and to the use of a naturally occurring omega conotoxin, such as GVIA, for treatment of diffuse axonal injury associated with human traumatic brain injuries (TBI) and spinal cord injuries (SCI).

BACKGROUND OF THE INVENTION

The predominant mechanism in most cases of traumatic brain injury (TBI) is diffuse axonal injury (Whyte and Rosenthal, 1993). While axonal injury is common in all TBI regardless of severity (Povlishock et al., 1992; Mittl, 1994), a shearing of the axons occurs in human diffuse axonal injury (DAI) leading to progressive changes that ultimately may result in the loss of connections between nerve cells. The slow progression of events in DAI continues for up to several weeks after injury creating a window of opportunity for therapeutic intervention.

There are approximately 500,000 new cases of TBI in the U.S. each year (Frankowski, 1985), and the incidence requiring hospitalization is estimated to be approximately 200-225/100,000 population (Frankowski, 1986; Cams, 1993). Currently, it is estimated that brain injuries account for 12% of all hospital admissions in the United States (Sandel, 1993). When compared to spinal cord injury, which accounts for less than 1% of hospital admissions, it is clear that TBI is a medical care problem which has a significant impact financially within the United States. Approximately 30,000-44,000 people will survive a severe TBI with GCS score<9 (Glasgow Coma Score Scale, Jennett, 1981) in the U.S. each year and more than 70,000 will be significantly disabled from moderate to severe TBI (GCS#10) (Whyte & Rosenthal, 1988). Yet with new medical management techniques, less than 10% will remain in a persistent vegetative state (Whyte, 1993; Rosner, 1992; Rosner, 1990). A GCS score of eight or less generally reflects a state of unconsciousness in which the patient demonstrates no eye opening, does not follow simple commands to move muscles, and has vocalizations which are limited to sounds. Such signs are indicative of severe brain injury (Whyte, 1993; Jennett, 1975, Jennett, 1981).

Approximately 52,000 to 56,000 people die each year from TBI (Kraus et al., 1996), resulting in direct costs approximated at more than $50 billion annually (Max et al., 1991). The costs of severe TBI to the individual and family are extremely high (McMordie, 1988). Acute medical and rehabilitation bills are often around $100,000 with some considerably higher (McMordie, 1988). The Model Systems Database for Traumatic Brain Injury demonstrates there is a correlation between the average Disability Rating Score and the combined acute care and rehabilitation charges (Bullock et al., 1995). Those with a severe TBI (GCS score of 6-8) have average combined charges of $110,842, and those with a very severe TBI (GCS score 3-5) have average combined charges of $154,256 (Lehmkuhl, 1993). About one-half of all TBIs are transportation related (Whyte, 1993; Lehmkuhl, 1993) and these patients have some of the highest combined charges for acute care and rehabilitations (Lehmkuhl, 1993). This may be related to the mechanism of TBI in high speed motor vehicle crashes, specifically the presence of diffuse axonal injury (DAI) being most prevalent in the midbrain and brain stem areas (Whyte, 1993). Clearly, brain injuries of this severity that occur with high speed acceleration-deceleration injuries, have the highest costs to society. TBI clearly causes more mortality, morbidity and probably more economic loss than HIV infection in the United States.

Motor vehicle crashes of all types are responsible for approximately 40%-50% of the TBI admissions recorded in the Model TBI Systems Database (Lehmkuhl, 1993). The predominant mechanism of injury is considered to be diffuse axonal injury (DAI). Approximately 30%-40% of the fatal head injuries involve diffuse axonal injury by pathological examination (Bennett et al., 1995; McLellan, 1990). However, based on beta-amyloid precursor protein immunostaining, axonal injury may be present in all cases of fatal head injury (Gentleman et al., 1995). In cases of persistent vegetative states, Kampfl et al. (1998) recently found that all cases had evidence of DAI in magnetic resonance imaging (MRI). Diffuse axonal injury occurs even in the absence of a blow to the head and is more prevalent than previously realized. Even in mild head injury, diffuse axonal injury is present in almost ⅓ of the cases (Mittl et al., 1994). The defining characteristic of DAI is the morphologic change to the axons which occurs over the course of several days to weeks and the fact that multiple regions of the brain are injured. While a component of DAI is present in blunt or penetrating trauma injury, it is at the periphery of the injury zone and is much less significant than the predominant mechanism of injury. DAI is the major mechanism of injury in high speed acceleration-deceleration injuries associated with motor vehicle crashes. While all four mechanisms of TBI (DAI, blunt trauma, penetrating trauma, axonia) may be involved in such an injury, it is the predominant mechanism of injury under this condition.

For human head injuries resulting from car collisions, the average velocity for the onset of severe injuries is 6.7 m/s (or 24.1 km/hour) as mentioned by Lorenzo et al. (1996). Most studies have been directed to the analysis of impact to the head. The Head Injury Criterion (HIC) is one method that is commonly used to assess the severity of an impact (Chou and Nyquist, 1974). Although it is considered to be the best available head injury indicator, a new finite element model using a dummy head has taken into account the effects of rotational and translational acceleration (Ueno and Melvin, 1995). Using this model, the dominant effect of translational acceleration was on principal stresses and rotational acceleration was on shear stresses.

Current research appears to point of plastic deformation within and of the axons that leads to the predominant cause of injury. The elastic tissues of the brain have plastic properties. Once the level of force is applied to a plastic substance, it is the time period over which it is applied that causes the amount of deformation. If the elastic memory of the substance is exceeded then there will be shearing and tearing. The high speed motor vehicle accident with deceleration lasting more than one to three seconds or several seconds of repetitive shaking can produce enough force for this to happen.

Materials research indicates that there is an amount of force which must be delivered below which plastic deformation of substances does not occur. In fact, the Gadd severity index initially attempted to measure the severity of injury utilizing an acceleration/time curve (Gadd, 1998). This critical amount of force appears to be essential in the development of injury (McLean & Anderson, 1997). This is very different from the contusive model of TBI where the forces are applied over milliseconds.

This indicates that once the amount of force has reached a threshold, it is the length of time the force is applied with the associated plastic deformation that is the predominant factor which causes the intracellular damage to the organelles within the axon. Hence, there is a continuum over which DAI occurs in TBI. After the threshold of necessary force to create plastic deformation is reached, it may be the length of time over which it is applied that determines the amount of DAI. This would explain the findings of Foda et al. (1994) where some DAI was noted in areas adjacent to a contusion injury in rats. Unfortunately, most TBI occurs over several seconds (high speed transportation crashes) where DAI is likely to be the predominant method of injury. This is supported by the fact that many severe TBI patients have minimal changes noted on CT scan following motor vehicle crashes.

Motor vehicle crashes are the predominant cause of DAI. A component of DAI is felt to be present in all motor vehicle crashes where the patient has lost consciousness (Whyte, 1988). For many years, DAI has been known to be associated with a coma of immediate onset after brain injury, but the diagnosis could only be established by autopsy. Indeed, the clinical syndrome of coma without any preceding lucid interval, decerebration, and autonomic dysfunction were often ascribed to primary brainstem injury. However, it is now clear that primary brainstem lesions do not occur in isolation but rather in association with DAI and usually involve the cerebral hemispheres and cerebellum in addition to the brainstem (McLellan, 1990). Evidence of the mechanism of injury can be elicited by pathological studies of patients killed from high speed transportation injuries (Pounder, 1997) as well as pathological studies of "shaken baby syndrome," a distinct subset of DAI (Nelson et al. 1993). A recent case report (Pounder, 1997) indicates that this shaking mechanism of DAI injury also applies to adults. The injury is characterized by specific neuropathological findings. On CT and MRI, this usually involves hemorrhagic punctate lesion of the corpus callosum, pontine-mesencephalic junction adjacent to the superior cerebellar peduncles and diffuse axonal damage in the white matter of the brain, brainstem and cerebellum which begin to atrophy within two weeks after injury (Whyte, 1988; Blumbergs, 1994).

Diffuse axonal injury in humans is characterized by widespread damage to axons in the cerebral hemispheres, the cerebellum and the brain stem and is a consistent feature of TBI (Adams, 1977; Adams, 1989; McLellan, 1990). The histological features of DAI depend on the length of time after injury, but within a day or so after injury there is evidence of damage to axons in the form of axonal bulbs. The initial findings are usually characterized microscopically utilizing neurofibrillar stains and stains for microglia which are abundant in the degenerating white matter. These findings are produced by the shear or flow of cytoplasm from the proximal end of a severed axon. Subsequently, the microscopic features correspond to Wallerian-type axonal degeneration as the axon disintegrates, which is probably due to metabolic disruption from injury and damage to the internal organelles from the lack of membrane integrity. In the first two years there is active myelin degeneration and in patients surviving longer, demyelination is the final stage of the process (McLellan, 1990). The result of the traumatic injury to the axons leads to the disconnection with various target sites, which is assumed to translate into the morbidity seen (Gennarelli, 1982; Povlishock, 1992). The severity of injury based on the histopathological changes has been graded in humans but not in experimental animals (Adams, 1977; Adam, 1989). The Adams classification (Adams, 1977; Adams, 1989) is used in human autopsy material, to classify the degree of DAI as mild, moderate or severe. In this classification, mild (grade 1) is characterized by microscopic changes in the white matter of the cerebral cortex, corpus callosum, and brain stem and occasionally in the cerebellum. Moderate (grade 2) is defined based on focal lesions in the corpus callosum. In severe (grade 3), there are additional focal lesions in the dorsolateral quadrants of the rostral brain stem (commonly in the superior cerebellar peduncle). This scheme has not been used for non-primate models because different regions of the brain are injured in the present models. However, it may be possible to apply this scheme to an appropriate model of DAI in small animals that is currently under development.

When a spinal cord injury or traumatic brain injury occurs, a cascade of damaging events begins which greatly increases the injury to the central nervous system (CNS). One basic factor that has been identified at the center of these events is calcium ($Ca^{++}$) ions.

Up to now, drugs have been used that are only marginally effective in preventing this cascade of events and non-steroidal inflammatory drugs (NSAIDS) have not been useful in animal models for neurotrauma. In part, this may be attributed to the fact that most NSAIDS also inhibit platelet function and consequently may increase bleeding. Furthermore, certain NSAIDS don't cross the blood brain barrier.

Recently there have been a few articles on the use of intrathecal NSAIDS for pain (Pain 1998, Southall et al.; *J. Pharmacol. and Exp. Ther.* 1997; 281:1381-91). Also, U.S. Pat. No. 5,914,129 to Mauskop discloses the use of magnesium containing analgesics for alleviation of pain such as from migraine headaches. Of these drugs aspirin, indomethacin, lysine clonixinate, and ketoprofen have been utilized. There have been no reports of intrathecal use in neurotrauma, for imparting neuroprotective effects, nor for the reduction or prevention of neuronal injury from inflammatory conditions. However, aspirin, which was probably the most potent and/or efficacious agent, could still inhibit platelets significantly. Aspirin crosses out of the CSF generally through the choroid plexus to the systemic circulation rather than the neural tissue. Even a baby aspirin a day is a potent inhibitor of platelets. Indeed, aspirin carries a considerable increased risk for intracerebral hemorrhage (Reymond et al. *Neurosurgery Reviews* 1992; 15:21-5). The inflammatory cascade that can be affected by NSAIDS include a reduction of arachidonic acid which initiates a metabolic cascade that produces inflammatory eicosanoids that promote neutrophil invasion and production of strong oxidants (Juurlink et al. *J. Spinal Cord Medicine* 1998; 21:309-34). This is most often by inflammatory leukotrienes. Even in the absence of enzyme activation arachidonic acid by the development of isoleukotrienes which are biologically active free radicals. Finally, NSAIDS reduce the production of inflammatory cytokines produced following CNS trauma which play a role in the development of secondary mechanisms of damage. NSAIDS reduce bradykinins and may reduce the production of platelet activating factor mediated induction of thromboxane $A_2$. These substances administered early on with cytokines and platelet activating factors may induce late regeneration of the axons and neurons, but it is clear they cause damage soon after injury.

In addition to the use of NSAIDs for treatment of neurotrauma, a new drug developed from the venom of a mollusk (conotoxin) that forms the conoshell has the potential to stop cascade initiated following traumatic brain injury or neurotrauma because it is directed at multiple calcium channels (pathways).

Limited success has been reported with drugs directed towards blocking the calcium channels but with untoward side effects. Furthermore, there appear to be many types of calcium channels that have been identified including L, N, P, Q, and T. Only L-type channel blockers have been marketed to reduce cerebral injury and these have had limited utility in only aiding in those with spontaneous intracerebral hemorrhage. However, there has been particular interest in blocking N-type channels.

Systemic delivery, via the blood stream, for example, of Ca-channel blockers has also been associated with problems in dropping the mean arterial pressure in trauma to the CNS. This results in a drop in the cerebral perfusion pressure. The cerebral perfusion pressure, defined as to the mean arterial blood pressure minus the intracranial pressure, is the physiologic variable that defines the pressure gradient driving cerebral blood flow and metabolite delivery, and is, therefore, closely related to central nervous system ischemia, the final point in the biochemical pathway that may double the amount of central nervous system injury from the initial injury.

The use of conotoxins for the treatment of neuronal damage related to an ischemic condition affecting the central nervous system is disclosed in U.S. Pat. No. 5,189,020 to Miljanich et al. ('020) issued Feb. 23, 1993. Miljanich et al. '020 disclosed the use of conotoxins in a method of treatment for reducing neuronal damage related to an ischemic condition in a human patient by administering a pharmacologically effective amount of a synthetic conotoxin to the patient. The method discloses the administration of the synthetic conotoxin via intracerebroventricular administration. However, it is well known that ischemic neural injury is very different from diffuse axonal injury or even direct trauma to the neurons with cell membrane disruption. Ischemic neural injury appears to involve different cellular mechanisms of injury. Additionally, Miljanich et al. disclose only L-type calcium channel blockers which have only been clearly successful in those conditions where there has been subarachnoid hemorrhage (*Neurology* 1998; 50:876-83) but not in traumatic brain injury without subarachnoid hemorrhage (*J. Neurosurgery* 1994; 80:797-804), or ischemic stroke (*Stroke* 1992; 23:3-8). Additionally, Miljanich et al. suggests that calcium channel blockers affect outcome by vasodilating the blood vessels; however, Applicants have discovered that the calcium channel blockers act directly on neurons as well.

Accordingly, it would be advantageous and desirable to have a method of treating the injuries associated with both traumatic brain injury and spinal cord injury (neurotrauma) by the intrathecal and/or intraventricular administration of non-steroidal anti-inflammatory drugs and/or by administering a natural omega conotoxin which interrupts the influx of extracellular calcium thereby both methods preventing or lessening the severity of CNS injury and which also overcomes the drawbacks and disadvantages of the prior art described above.

SUMMARY OF THE INVENTION

According to the present invention, there is disclosed a method for treating a patient/subject having pain, neurotrauma or traumatic brain injury such as diffuse axonal injury, which includes administering to the subject a therapeutically effective amount of a non-steroidal anti-inflammatory drug, a natural omega conotoxin or functional fragment thereof or a combination thereof.

BRIEF DESCRIPTION OF THE DRAWINGS

The following detailed description is best understood with reference to the following drawings in which.

DETAILED DESCRIPTION OF THE INVENTION

Figures 1, 2:
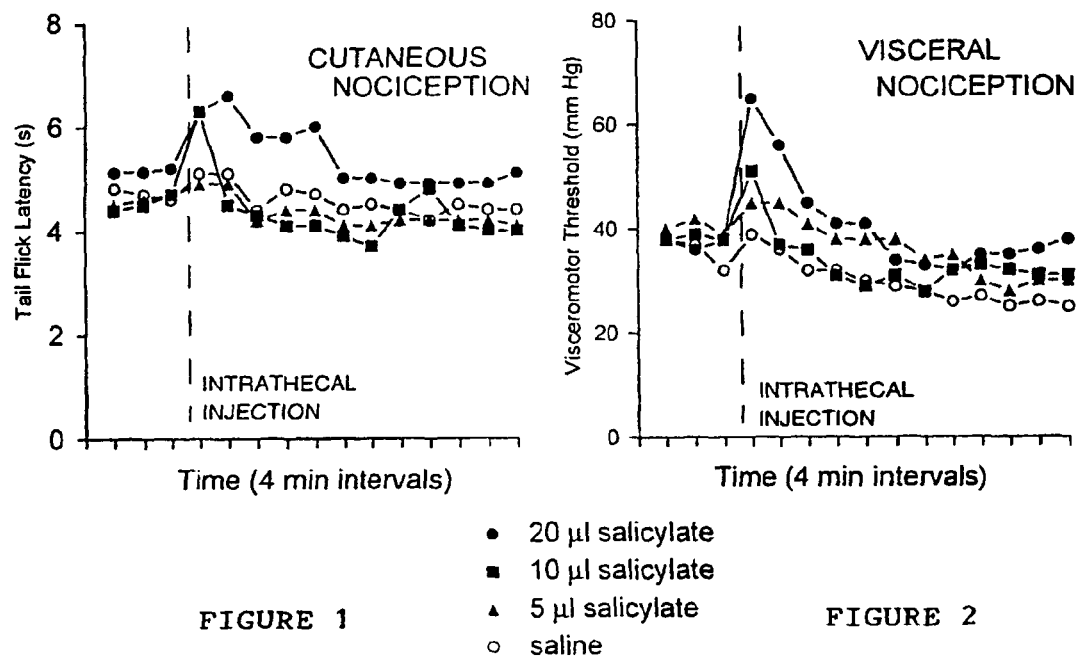
FIG. 1 is a graph illustrating cutaneous nociception results.
FIG. 2 is a graph illustrating visceral nociception results.

The present invention provides a method for treating neuronal injuries, diseases, conditions, disorders, pain including neurogenic pain, neuronal injury caused by inflammatory conditions, or neurotrauma often associated with traumatic brain injury (TBI) and/or spinal cord trauma (SCT), including diffuse axonal injuries manifested in conditions such as dystonia/spasticity, spastic disorders, convulsive disorders, or epilepsy by intrathecally and/or intraventricularly administering directly into the cerebrospinal fluid (CSF) of a patient or subject having or suspected of having or developing diffuse axonal injuries a therapeutically effective amount of a non-steroidal anti-inflammatory drug and/or a naturally occurring omega conotoxin, functional fragment thereof, pharmacologically acceptable salts, esters, amides, and prodrugs thereof.

The terms "patient" and "subject" mean all animals including humans. Examples of patients or subjects include humans, cows, dogs, cats, goats, sheep, and pigs.

The term "functional fragment thereof" means a fragment or portion of the native conotoxin which retains the desired function(s) of the native conotoxin which are desirable for the treatment of diffuse axonal injury associated with either traumatic brain injury or spinal cord injury.

Those skilled in the art are easily able to identify patients or subjects having diffuse axonal injuries including conditions such as dystonia/spasticity, spastic disorders, convulsive disorders, and epilepsy. For example, patients who have sustained traumatic brain injury induced dystonia/spasticity. Additionally, patients or subjects having pain or inflammatory conditions affecting the nervous system such as Lupus and other inflammatory neuropathies, infections, acquired disorders such as multiple sclerosis, transverse myelitis, Parkinson's disease, CNS vasculitis, and Alzheimer's disease.

A therapeutically effective amount is an amount of the non-steroidal anti-inflammatory drug and/or the naturally occurring omega conotoxin or functional fragment thereof that when administered to a patient or subject, ameliorates a symptom of the condition or disorder.

Studies are demonstrating that there will be reduced injury at the site of neurologic lesion, particularly those areas that would be most proximal to the flow of CSF. These areas of the CNS include those injured during high speed motor vehicle crashes associated with diffuse axonal injury (DAI), which accounts for 50% of TBI, anoxic TBI (oxygen deprivation to the brain) and most cases of SCI.

The delivery system selected to deliver this drug (intrathecal or intraventricular catheters) eliminates side effects, particularly a drop in blood pressure that would negate the cellular protective effects. Drops in blood pressure have been linked to further injury and more chronic deficits in spinal cord injury. Placement of the catheter close to the site of injury will allow local concentration of the medication at a higher level than obtained by other delivery routes.

This delivery method (pointed to different points of the CNS and using different techniques (methods) for insertion and subsequent utilization) is already being used in humans to treat spasticity, and to deliver drugs to improve function from Parkinson's disease.

The compounds of the present invention can be administered to a patient either alone or as part of a pharmaceutical composition. The compositions can be administered to patients either intrathecally or intraventricularly.

Compositions suitable for intrathecal or intraventricular delivery may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyloleate. Proper fluidity can be maintained, for example, by the use of a coating such as lecithin, by the maintenance of the required particle size in the case of dispersions, and by the use of surfactants.

In a preferred embodiment, the non-steroidal anti-inflammatory drugs include choline-magnesium trisalicylate, sodium salicylate, salicylamide, other non-acetylated aspirins, analogs, substituted forms, derivatives and/or any pharmaceutically acceptable salt, ester, amide, and prodrug thereof.

The term "substituted" means that the base organic radical has one or more substituents.

In a preferred embodiment, the naturally occurring omega conotoxin or functional fragment thereof administered to a patient or subject are naturally occurring omega conotoxins known as GVIA and MVII, both of which N-type calcium channel blockers.

In addition to the intrathecal or intraventricular administration of the naturally occurring omega conotoxin or functional fragment thereof for the treatment of diffuse axonal injury associated with traumatic brain injury or traumatic spinal cord injury, a non-steroidal anti-inflammatory drug (NSAID) can be combined with the naturally occurring omega conotoxin, preferably an N-type calcium channel blocking omega conotoxin, to further reduce the amount of neurological injuries in a patient sustaining neurological injury such as that associated with traumatic brain or spinal injury, i.e., diffuse axonal injury.

The NSAIDS which are suitable for use in combination with the omega conotoxin include sodium salicylate, salicylamide, choline magnesium trisalicylate and other deacetylated aspirins.

Injury to the areas of the brain or spinal cord contiguous to the flow of CSF can be significantly protected by direct delivery of the compounds of the present invention to the CSF early after injury via intraventricular catheters. Delivery and access can be achieved with a catheter such as that disclosed in PCT Application Serial No. PCT/US00/05740, to Applicant, for safety and efficacy.

One study of the intrathecal delivery of NSAIDS on pain fibers in rats required an equivalent dose of 140 mg in humans (Bustamante et al. *J. Pharmacology and Experimental Therapeutics* 1997; 281:P1381-91). There are two non-acetylated aspirins which do not inhibit platelets and which are still potent NSAIDS, these are salicylate and choline-magnesium trisalicylate. The latter is very water soluble and is a choline-magnesium salicylate while the former is not. Additionally magnesium may have neuroprotective effects as well as blocking N-methyl-D-aspartase (NMDA) channels in a voltage dependent manner (Mayer et al. *Nature* 1984; 309:261-3; Nowak et al. *Nature* 1984; 307:462-5) thereby interrupting a well known pathway for cell death.

The drugs above are easily dissolved in aqueous solution and are able to cross-over to the CNS. The NSAIDS are also cleared easily from the CNS. Furthermore, choline-magnesium trisalicylate apparently causes no more gastric problems than a placebo (PDR, 1999 Disalcid, Trilisate descriptions). All of the above listed compounds are water soluble and should reduce the amount of neurological injury whether induced by trauma, ischemia, hemorrhage, tumors, or inflammatory conditions to the affected areas that are contiguous to delivery in the CSF. This would include inflammatory conditions such as cerebral vasculitis and cerebral sarcoid.

It has been clearly demonstrated that following head injury, traumatic brain injury, and spinal cord injury, that prostaglandin synthesis increases (Shohami et al. *J. Cerebral Blood Flow and Metabolism* 1987; 7:58-63). Therefore, other inflammatory factors should respond to NSAIDS if delivered quickly and to the right location. However, all of these prior studies have failed because the drugs used affected platelets thereby inactivating them.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatine.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Barge et al., "Pharmaceutical Salts," *J. Pharm. Sci.,* 1977, 66:1-19 which is incorporated herein by reference.)

Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$-$C_3$ alkyl primary amines, and $C_1$-$C_2$ dialkyl secondary amines are preferred. Amides of the compounds of the invention may be prepared according to conventional methods.

The term "prodrug" refers to compounds that are rapidly transformed in vivo to yield the parent compounds of the above formula, for example, by hydrolysis in blood. A thorough discussion is provided in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the NSAIDs and/or omega conotoxins of the present invention can exist in unsolvated as well as solvated forms with pharmaceutically acceptable sol vents such as water, ethanol, and the like. In general, the solvated forms are considered equivalent to the unsolvated forms for the purposes of the present invention.

The NSAIDs of the present invention can be administered to a patient at dosage levels in the range of about 100 mg to about 1500 mg per day. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The naturally occurring omega conotoxins and/or the NSAIDs can be intrathecally or intraventricularly administered utilizing an intraspinal catheter. The intraspinal catheter is disposed within the spinal subarachnoid space in the thoracolumbar and sacral spinal regions. Since intrathecally delivered omega conotoxin can quickly cross out of or pass out of the intrathecal space to the spinal cord, in those patients with dystonia/spasticity involvement of the upper extremities, the medical provider inserting the catheter may wish to insert the intraspinal catheter more cephalid. Meythaler et al., *Perspectives in Neurosurg.* 1996; 7(2):99-107. A similar effect has been shown for intrathecal baclofen where the catheter was threaded more cephalid than the T-10 level which was found to improve sustained response in the upper extremity tone. Meythaler et al., *J. NeuroSurgery* 1997; 87:415-9; Meythaler et al., *Am J. Phys. Med. Rehabil.* 1998; 77-173.

As stated above, both the intrathecal and intraventricular administration of the NSAIDs and/or the omega conotoxins can be supported utilizing an implantable pump.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

EXPERIMENTAL

Intrathecal Salicylate for Pain

Two rats with chronic spinal cord injury were chosen because they consistently exhibited allodynia. A 1-French silicon tubing was threaded into the intrathecal space from the atlanto-occipital membrane. The intrathecal catheter was connected an ESOX that was implanted subcutaneously. The ESOX pump flowed at a rate of 60 µl per day. Initially, saline was placed in the pumps. At testing on days 2, 12, 14 after pump placement, signs of allodynia were consistently observed when the animals were lightly touched at particular parts of their body (left flank for rat 1 and right shoulder for rat 2). Animals vocalized consistently when these areas were lightly touched. All of the behavioral testing was done by a person who was unaware of the type of drug delivered or the expected effects of the drug. The saline was removed from the pumps and the pumps were refilled with salicylate. On repeated tested of these animals, no evidence of allodynia was observed. When the salicylate was removed and replaced with saline, consistent allodynia was observed.

Intrathecal Salicylate for Treatment of Acute and Persistent Pain

Methods:

GENERAL: Male Sprague-Dawley rats were deeply anesthetized with a mixture of halothane and oxygen and an intrathecal catheter was placed at the level of the lumbar enlargement of the spinal cord using sterile technique and the method of Yaksh and Rudy. The surgical area was closed leaving the distal end of the catheter accessible for bolus injections. Group 1 (acute pain, cutaneous and visceral) rats were allowed to recover overnight and Group 2 (persistent pain, formalin test) rats allowed to recover for one week prior to further testing. Rats were not used if there was evidence of neurological deficit.

Group 1 (acute pain, cutaneous and visceral) Protocol: Rats were assigned to one of four subgroups (n=5-6/subgroup). On the day of testing these rats were lightly anesthetized with inhaled halothane (0.5-0.8%) in oxygen delivered by facemask and baseline responses obtained for the tail flick test and the colorectal distension test. Each subgroup them subsequently received a 20 ml bolus dose of Choline-Mg-Salicylate (0, 2.5, 5 or 10 mg using a 500 mg/ml solution) and/or normal saline. These rats were then was tested using both the tail flick and colorectal distension tests at four minute intervals beginning one minute after the bolus dose. The tests used are given below and the results are shown in FIGS. 1 and 2.

Tail flick Test (cutaneous nociception, FIG. 1): The tail of the lightly anesthetized rat was placed on the testing apparatus and a 1.5×11 mm area of the ventral surface of the middle third of their tail exposed to radian heat (projector bulb). The tail flick latency was defined as the latency from the onset of tail heating movement to the flexion-withdrawal reflex movement of the tail as determined using a photoelectric device and measured to the nearest 0.1 second. The tail was removed from heat if there was no movement within eight seconds to avoid damage to the tail.

Colorectal distension Test (visceral nociception, FIG. 2): The visceromotor response is a reflex contraction of the abdominal and hindlimb musculature in response to slowly increasing pressure within a distending balloon in the colon and rectum. Air is used to inflate a 7-8 cm flexible latex balloon catheter (end of balloon 1 cm from the anus) inserted via the anus and kept in position by taping the catheter to the base of the tail. Pressure within the balloon was measured using an in-line manometer. The threshold for response is defined as the minimal amount of pressure within the distending balloon, which produces a visible contraction.

Group 2 (persistent pain, formalin test) Protocol: Rats were briefly anesthetized with inhaled halothane (2%) in oxygen. The intrathecal catheters were accessed and 0 or 10 mg (of a 500 mg/ml solution of CMS) was injected followed by a 10 ml normal saline flush. 50 ml of a solution of 5% formalin was injected into the dorsum of the right hindpaw and the rat allowed to recover from anesthesia. The rat was then observed for the next hour and the number of flinches/licks of the hindpaw measured for one minute at five minute intervals.

Results:

Choline-Mg-Salicylate produced an effect in all three models of nociception. In the tail flick and colorectal distension tests the response was demonstrated to be dose-dependent. In those tests the response to the bolus was rapid in onset suggesting that there was either a nonspecific effect of the compound or that CMS crosses from the CSF into the spinal cord quickly. The effects were not long-lasting suggesting that continuous intrathecal delivery is an effective method for intrathecal administration.

Intrathecal Salicylate to Prevent Secondary Damage and Inflammation Following Spinal Cord Injury In this study, twenty-four rats deeply anesthetized rats received a moderate to severe spinal cord injury using a 2-French Fogarty embolectomy catheter. Shortly after injury, a 1-French silicon tubing was threaded into the intrathecal space from the atlanto-occipital membrane. The intrathecal catheter was connected an ESOX that was implanted subcutaneously. The ESOX pump flowed at a rate of 60 µl per day. Animals were randomly assigned to receive saline or salicylate. Animals were tested each week using the BBB locomotor test. All of the behavioral testing was done by a person who was unaware of the type of drug delivered or the expected effects of the drug. Animals that received the salicylate exhibited on average less functional deficits. The average score for the saline treated rats was 0 while the average score for salicylate treated rats was 5.45.

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which define the scope of the invention.

Any patents, applications, or publications mentioned in the specification are indicative of the levels of those skilled in the art to which the invention pertains. These patents, applications, and publications are herein incorporated by reference to the same extent as if each individual publication was specifically and individually indicated to be incorporated by reference.

The invention claimed is:

1. A method for treating a subject having inflammation associated with neurotrauma, said method comprising intrathecally administering by intrathecal catheter to the subject a therapeutically effective amount of choline magnesium trisalicylate or prodrug thereof non-inhibitory of platelets so as to reduce the inflammation associated with the neurotrauma.

2. A method according to claim 1, wherein said therapeutically effective amount of choline magnesium trisalicylate further comprises a deacetylated aspirin.

3. A method for treating a subject having inflammation associated with neuronal injury, said method comprising intrathecally administering by intrathecal catheter to the subject a therapeutically effective amount of choline magnesium trisalicylate or prodrug thereof that is non-inhibitory of platelets so as reduce the inflammation associated with the neuronal injury.

4. A method according to claim 3, wherein therapeutically effective amount of choline magnesium trisalicylate further comprises a deacetylated aspirin.

5. A method according to claim 3, wherein the neuronal injury is caused by Lupus, inflammatory neuropathy, infection, transverse myelitis, Parkinson's disease, CNS vasculitis, or Alzheimer's disease.

6. A method for treating a subject having inflammation associated with neurotrauma, said method comprising intraventricularly administering by intraventricular catheter to the subject a therapeutically effective amount of choline magnesium trisalicylate or prodrug thereof non-inhibitory of platelets so as to reduce the inflammation associated with the neurotrauma.

7. A method according to claim 6, wherein therapeutically effective amount of choline magnesium trisalicylate further comprises a deacetylated aspirin.

* * * * *